United States Patent [19]
Malamud et al.

[11] Patent Number: 5,928,195
[45] Date of Patent: Jul. 27, 1999

[54] REMOTE CONTROL DRUG DELIVERY DEVICE

[76] Inventors: Daniel Malamud, 430 Sycamore Ave., Merion, Pa. 19066; Mitchell Litt, 240 S. 33rd St., Philadelphia, Pa. 19104; Benjamin L. Lewis, 420 E. 85th St.—Apartment 3 Rear, New York, N.Y. 10028

[21] Appl. No.: 09/123,299

[22] Filed: Jul. 28, 1998

Related U.S. Application Data

[63] Continuation of application No. PCT/US97/01871, Jan. 31, 1997
[60] Provisional application No. 60/010,893, Jan. 31, 1996.

[51] Int. Cl.[6] .................................................. A61M 5/155
[52] U.S. Cl. ............................................. 604/141; 604/891.1
[58] Field of Search ................................. 604/891.1, 141, 604/131, 151, 890.1

[56] References Cited

U.S. PATENT DOCUMENTS

| | | | |
|---|---|---|---|
| 3,640,277 | 2/1972 | Adelberg | 604/141 |
| 3,756,459 | 9/1973 | Bannister et al. | 604/141 |
| 4,265,241 | 5/1981 | Portner et al. | 604/141 |
| 4,299,220 | 11/1981 | Dorman | 604/141 |
| 5,163,909 | 11/1992 | Stewart | 604/131 |
| 5,242,406 | 9/1993 | Gross et al. | 604/141 |
| 5,348,539 | 9/1994 | Herskowitz | 604/141 |
| 5,433,704 | 7/1995 | Ross et al. | 604/141 |
| 5,553,741 | 9/1996 | Sancoff et al. | 604/141 |
| 5,700,245 | 12/1997 | Sancoff et al. | 604/141 |
| 5,810,015 | 9/1998 | Flaherty | 604/141 |

*Primary Examiner*—Paul J. Hirsch
*Attorney, Agent, or Firm*—Panitch Schwarze Jacobs & Nadel, P.C.

[57] ABSTRACT

A remotely controlled drug delivery device administers a dose of a drug, agent or microbicide using a gas pressure delivery system. The device stores multiple doses of the drug or agent. A toroid shaped housing includes three chambers, a gas chamber containing a pressurized gas, a drug storage chamber containing the drug or agent, and an expandable chamber for delivering the drug from the drug storage. The device includes an electronic controller for opening a valve connecting the gas chamber to the expandable chamber for a predetermined period of time in order to deliver a predetermined dose of the drug. The controller communicates with a remote control device via radio frequency. The remote control device sends a signal to the controller, which causes a dose to be delivered. The controller returns a signal to the remote control device indicating that the dose has been delivered and a signal indicating when the device needs to be removed for maintenance. The device may be used in any body cavity to deliver any desired type of drug.

31 Claims, 2 Drawing Sheets

REMOTE CONTROL DRUG DELIVERY DEVICE

CROSS-REFERENCE TO RELATED APPLICATION

This application claims the benefit of U.S. Provisional Patent Application No. 60/010,893 filed Jan. 31, 1996 an a continuation of PCT/US97/01871 filed Jan. 31, 1997.

BACKGROUND OF THE INVENTION

The present invention relates to remotely activated drug delivery systems and more particularly, to a remotely activated intravaginal drug delivery device.

Body implantable devices that release drugs are known in the prior art. Generally, such devices provide for either a single release, or a single, continuous release of a drug into the body. However, certain body implantable devices are also known which are capable of providing periodic releases of a drug into the body. For instance, U.S. Pat. Nos. 5,167,625 and 5,318,557 each discloses an implantable drug delivery device which uses gas pressure to force a dose of a drug into the body upon command. However, each of these references discloses a gas generation system which generates gas upon demand. Such gas generation systems include a number of drawbacks, including the inability to adequately control the volume and speed of the outflow of the drug and the lack of sufficient feedback to ensure a dose of the drug was delivered. In contrast, the present invention provides a drug delivery device having a preloaded, gas pressurized chamber and a controlled valve for controlling the pressure forces used to deliver a dose of the drug.

The present invention includes a remotely activated electronic control circuit for administering delivery of a dose of a drug. In a preferred embodiment, the present invention provides a vaginal ring or other shape housing which is capable, upon receiving a remote command, of periodic release of a drug into the body. With the proper drug, agent, or microbicide, the present invention provides protection from or treats sexually transmitted diseases (STDs), including herpes, syphilis, gonorrhea, chlamydia and HIV. In addition, the device may be used to deliver a contraceptive drug. Many microbicides are also themselves spermicidal, to provide both treatment and contraceptive functions. The novel drug delivery device is discreet, safe and effective.

SUMMARY OF THE INVENTION

Briefly stated, the present invention is a drug delivery system comprising a housing, a drug storage chamber having at least one exit port, the drug storage chamber located within the housing for holding at least one predetermined dose of a predetermined drug, a drug delivery chamber disposed within the drug storage chamber, a gas pressurized chamber located within the housing for holding a gas under pressure, a valve connecting the gas pressurized chamber with the drug delivery chamber, the valve having an open position and a closed position, wherein in the open position, the gas is delivered through the valve to the drug delivery chamber, a remotely activated control circuit electrically connected to the valve, the control circuit for receiving a remotely generated valve open signal and generating an electrical valve open signal therefrom, and providing the electrical valve open signal to the valve, and a signaling device spaced from the control circuit for transmitting the remotely generated valve open signal to the control circuit, wherein upon receipt of the electrical valve open signal, the valve opens such that the gas in the gas pressurized chamber is released into the drug delivery chamber, thereby forcing a predetermined dose of the drug into the at least one exit port and out of the housing.

The present invention is also directed to a drug delivery system comprising:

a housing;

a drug storage chamber located within the housing and having at least one exit port, the drug storage chamber adapted for holding at least one predetermined dose of a predetermined drug;

a drug delivery chamber disposed within the drug storage chamber;

a gas pressurized chamber located within the housing for holding a nontoxic gas under pressure;

a valve connecting the gas pressurized chamber with the drug delivery chamber, the valve having an open position and a closed position, wherein in the open position, the gas is delivered through the valve to the drug delivery chamber, thereby forcing one dose of the drug out of the exit port;

a pressure transducer located within the gas pressurized chamber for monitoring the gas pressure therein and generating a corresponding gas pressure signal;

a signaling device spaced from the housing for generating a valve open signal and transmitting the valve open signal at a predetermined radio frequency; and a remotely activated control circuit located within the housing, the control circuit including a receiver circuit, a timer circuit, and a transmitter circuit, the receiver circuit for receiving the transmitted valve open signal, the timer circuit receiving the transmitted valve open signal from the receiver circuit, generating an electrical valve open signal, and providing the electrical valve open signal to the valve for a predetermined time period, and the transmitter circuit for receiving the gas pressure signal from the pressure transducer, generating a dose delivered signal therefrom, and transmitting the dose delivered signal to the signaling device, wherein the signaling device includes a display for displaying the dose delivered signal.

The present invention is further directed to an intravaginal drug delivery device comprising:

a generally toroid shaped housing sized to fit within a human vagina;

a drug storage chamber located within the housing and having at least one exit port, the drug storage chamber for holding a plurality of predetermined doses of a predetermined drug;

a drug delivery chamber comprising a flexible, expandable membrane disposed within the drug storage chamber;

a gas pressurized chamber located within the housing for holding a nontoxic gas under pressure;

a valve connecting the gas pressurized chamber with the drug delivery chamber, the valve having an open position and a closed position, wherein in the open position, the gas is delivered through the valve to the drug delivery chamber;

a pressure transducer located within the gas pressurized chamber for monitoring the gas pressure therein and generating a corresponding gas pressure signal;

a signaling device spaced from the housing generating a valve open signal and transmitting the valve open signal at a predetermined radio frequency; and a remotely activated control circuit located within the housing, the control circuit including a receiver circuit, a timer circuit, and a transmitter circuit, the receiver circuit for receiving the transmitted valve open signal, the timer circuit receiving the transmitted valve open signal from the receiver circuit, generating an electrical valve open signal, and providing the electrical valve open signal to the valve for a predetermined time period, and the transmitter circuit for receiving the gas pressure signal from the pressure transducer, generating a dose delivered signal therefrom, and transmitting the dose delivered signal to the signaling device, wherein the signaling device includes a display for displaying the dose delivered signal.

BRIEF DESCRIPTION OF THE DRAWINGS

The foregoing summary, as well as the following detailed description of preferred embodiments of the present invention, will be better understood when read in conjunction with the appended drawings. For the purpose of illustrating the present invention, there is shown in the drawings an embodiment which is presently preferred. It should be understood, however, that the present invention is not limited to the particular arrangement and instrumentalities shown. In the drawings.

DETAILED DESCRIPTION OF THE INVENTION

Figure 1:
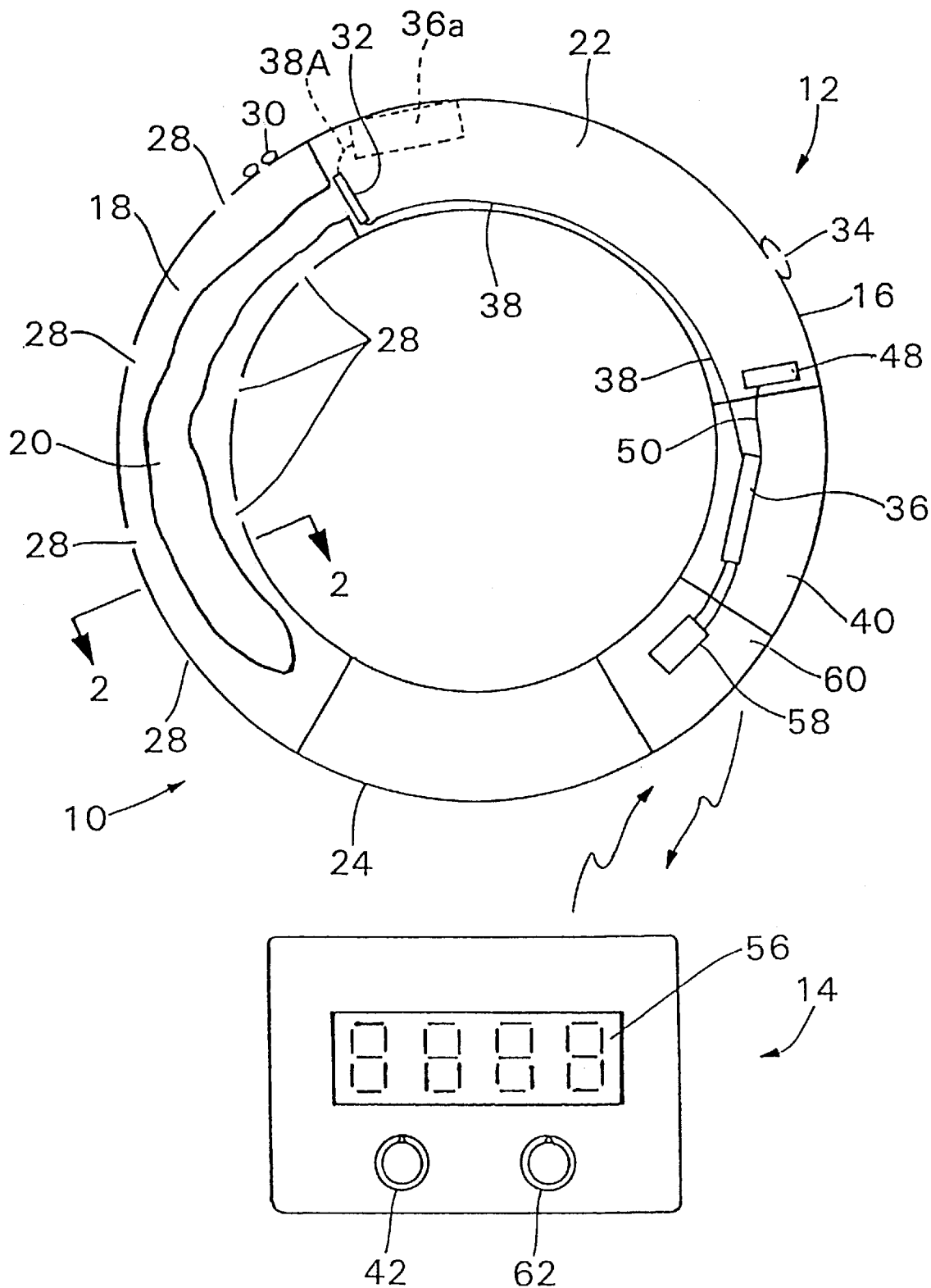
FIG. 1 is an enlarged plan view partially in cross-section of a drug delivery system in accordance with a preferred embodiment of the present invention.

Certain terminology is used in the following description for convenience only and is not limiting. The words "top", "bottom", "lower" and "upper" designate directions in the drawings to which reference is made. The terminology includes the words above specifically mentioned, derivatives thereof and words of similar import.

The present invention is directed to a remote controlled drug delivery system. In a preferred embodiment, the system comprises a toroidal shaped housing sized to fit within a human vagina and a remote control device. The housing includes at least three chambers: (1) a drug storage chamber, (2) a drug delivery chamber, and (3) a gas pressurized chamber. In addition, an electronic control circuit is disposed within the housing. The remote control device is provided for transmitting signals to and receiving signals from the electronic control circuit. The remote control device permits a user to administer a dose of a drug stored within the housing and also to determine whether the dose has been delivered. In the presently preferred embodiment, the drug delivery system comprises an intravaginal device for administering a predetermined drug, such as a microbicide.

Referring now to the drawings in detail, wherein like numerals indicate like elements throughout the several views, there is shown in FIG. 1 an enlarged plan view partially in cross-section of an exemplary drug delivery system 10 in accordance with a preferred embodiment of the present invention. The drug delivery system 10 is described herein with reference to delivering a microbicide to a human by inserting or implanting a drug delivery device within a body cavity (e.g., a vagina). However, it will be understood by those of ordinary skill in the art that the system 10 can be used to deliver other types of drugs in various other portions of the body (both natural cavities and in surgically implanted areas) and that the system 10 can be used by both humans (males and females) and animals.

The drug delivery system 10 includes a drug delivery device 12 and a remote signaling or control device 14. The drug delivery device 12 contains a predetermined number of doses of a predetermined drug and the remote signaling device 14 allows a user or patient to administer a dose of the drug within the body where the delivery device 12 is located. The user of the remote signaling device 14 may be the person in whose body the device 12 is located or a care giver to one in whose body the device 12 is disposed.

Figure 2:
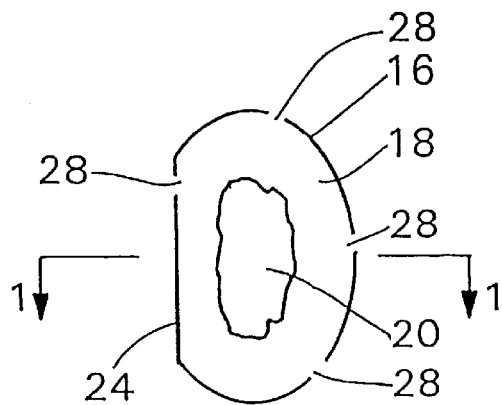
FIG. 2 is an enlarged cross-sectional view of a device of the drug delivery system of FIG. 1, taken along lines 2—2 of FIG. 1.

The drug delivery device 12 is shown in FIGS. 1 and 2. FIG. 2 shows an enlarged cross-sectional view of the device 12 taken along lines 2—2 of FIG. 1 and FIG. 1 shows an enlarged partial cross-sectional view of the device 12 taken along lines 1—1 of FIG. 2. The drug delivery device 12 comprises a housing 16 having at least three chambers: (1) a drug storage chamber 18, (2) a drug delivery chamber 20, and (3) a gas pressurized chamber 22. In the presently preferred embodiment, the housing 16 is sized to fit within a cavity of a human body, such as a vagina, and shaped to be easily inserted and removed from the body cavity. Accordingly, in the presently preferred embodiment, the housing 16 is generally toroidal or ring shaped. The toroidal shaped housing 16 has an outer diameter of about 40 mm to about 80 mm and a thickness of about 7 mm to about 15 mm, resulting in an inner diameter of about 25 mm to about 75 mm. According to the presently preferred embodiment, the toroidal shaped housing 16 is sized to fit within a human vagina such that the device 12 occupies a space within the vagina. The device 12 may occupy a variety of locations within the vagina and preferably does not interfere with sexual intercourse.

Referring now to FIG. 2, the housing 16 has a generally oval cross-section, although other cross-sections, such as circular or any other shape may also be used. An exemplary housing 16 may have an outer diameter of about 60 mm and an inner diameter of about 50 mm. One advantage of the toroidal shape is that it permits the drug delivery device 12 to be easily inserted and removed from the vagina by a patient or user, and thus, the device 12 need not be inserted or removed by a doctor, nurse or medical specialist. For example, a finger may be inserted into the hole defined by the inner diametrical wall in order to facilitate installation, positioning and removal of the housing 16 from the vagina. Moreover, since ring shaped vaginal devices are known for other applications, a person may have less apprehension of using the device 12. The device 12 is preferably inserted in the back of the vagina much like a diaphragm or cervical cap.

Although preferably ring shaped, the housing 16 could comprise other shapes and still be easy to install and remove from a body cavity. For instance, the housing 16 could be cylindrical and include a hook, loop or ring which may be gripped by a finger or a medical tool such that the housing 16 is easy to install and remove from a body cavity. Alternatively, the housing 16 could comprise two parallel hollow rods which are connected by arches at the ends. Thus, although the housing 16 is shown and described as toroidal shaped, the invention is not to be limited to such shape.

Preferably, the housing 16 is constructed of a non-conductive, flexible, biocompatible material, such as a medical grade silicone approved for internal use by the U.S. Food and Drug Administration (FDA). Such material is generally commercially available, such as Dow Chemical's Silastic Medical Grade 382 or a similar type material supplied by Applied Silicon Co., of Ventura, Calif. It is preferred that the housing 16 be flexible so that the housing 16 or portions thereof may be bent, folded, collapsed, or otherwise deformed for insertion within a body cavity, and after insertion, the housing 16 returns to its original shape. The housing 16 is also sized and shaped such that it is not uncomfortable for the user or patient and does not inhibit the user from performing normal activities, such as intercourse. Ideally, once inserted, the user is not physically aware of the presence of the device 12 and the device 12 may be worn indefinitely, but generally should be removed during menstruation.

Referring now to FIGS. 1 and 2, the drug storage chamber 18 comprises a generally hollow section of the housing 16 for holding or storing a predetermined amount of a predetermined drug. Preferably, the predetermined amount comprises at least one predetermined dose of the drug, and preferably a plurality of doses of the drug, such as between 10 and 30 doses. However, more or fewer doses of the drug may be stored in the drug delivery chamber 18, depending upon a number of factors, such as the type of drug, the shelf life of the drug, the composition of the drug, and the size of a dose. The drug storage chamber 18 is sized to store the desired predetermined amount of the drug. For instance, a size sufficient to store approximately 5.0 cc of a drug is envisioned. Of course, as will be understood by those of ordinary skill in the art, the size of the drug storage chamber 18 may be made to account for the type and potency of the particular drug to be used with the device. Moreover, the drug storage chamber 18 need not be filled to its maximum capacity with any given drug.

For an intravaginal microbicide device, the preferred drug may comprise a surfactant with spermicidal, antiviral, antibacterial, and antifungal activities, such as a class of compounds comprising as a first component an alkyl-N-betaine surfactant and as a second compound an oxide selected from the group consisting of alkyl-N, N-dimethyl amine oxide, N-dihydroxyethylamine oxide, acylamino t-amine oxide and mixtures thereof, as disclosed in U.S. Pat. Nos. 4,107,328, 4,839,158 and 5,314,917, the disclosures of which are hereby incorporated herein by reference. The preferred compound within this class is known as "C31G" and contains alkyl dimethyl glycine and alkyl dimethyl amine oxide. It is believed that a general application of this class of compounds and specifically C31G in the vagina is sufficient to be effective as a spermicide and/or anti-STD agent with antiviral and antibacterial qualities. Generally, a dose of the drug will disperse throughout the vagina in about one to two minutes, although such dispersion time is generally not critical, especially in view of the length of time the drug remains active. Also, the dispersion time may vary depending upon the drug used and the location of the drug delivery device 12. In the preferred embodiment, it is preferred that a delivered dose of the drug remains effective for at least six to eight hours, without douching. Of course, other drugs may be used with the present invention, as will be understood by those of ordinary skill in the art. For instance, nonoxynol-9 or octoxynol-9 could also be used as spermicidal surfactants. Any other type of microbicide could also be used, such as sulfated polysaccharides, chlorhexidine or benzylalkonium chloride, for example.

In determining an amount of drug required for each dose, concentration calculations are based on the use of the minimum effective amount of each dispersed dose. In order to provide a device 12 capable of administering 30 doses of C31G with an average volume of 0.16 cc, the total volume of the drug storage chamber 18 is about 4.8 cc. However, it will be understood by those of ordinary skill in the art that the present invention may be implanted in other locations of a body and used to administer other drugs, such as hormones, vitamins, antibiotics, fungicides, anticoagulants, cancerocidal agents, vasoactive agents, any other substances used to control, treat, diagnose, or otherwise affect physical or mental conditions.

The drug storage chamber 18 further comprises at least one exit port, as schematically illustrated by exit port 28, and preferably a plurality of exit ports 28 through which the drug is dispersed from the drug storage chamber 18 and the housing 16 to the body cavity. The exit ports 28 are one-way ports which permit the drug, when subject to sufficient pressure, to be ejected or dispersed from the drug storage chamber 18 out of the device 12. Such one-way ports or valves are known to those of ordinary skill in the art. For instance, a nipple type exit port may be used. The exit ports 28 are located around the periphery of the drug storage chamber 18 for optimal distribution of the drug. The exit ports 28 may be located all on an outer wall 24 of the housing 16, on a top or bottom of the housing 16, or at each of these locations, as shown. The drug storage chamber 18 and the exit ports 28 are designed to be leak proof in order to prevent the drug stored in the chamber 18 from leeching or otherwise escaping from the chamber 18 except when desired. Alternatively, the exit ports 28 could comprise a plurality of slits in the drug storage chamber 18, which allow the drug to pass through therethrough only when sufficient pressure is exerted on the drug to force the drug through the slits.

The drug storage chamber 18 may optionally also include a drug receiving port 30 through which the drug may be inserted into the drug storage chamber 18, such that the device 12 may be filled with the drug and also refilled upon depletion of the drug. For instance, a needle of a syringe (not shown) could be received by the receiving port 30 for refilling the drug within the chamber 18.

The drug delivery chamber 20 comprises a sealed chamber disposed within the drug storage chamber 18. The drug delivery chamber 20 preferably comprises an inflatable, expandable membrane which, when expanded, exerts a pressure force on the drug within the drug storage chamber 18 sufficient to force a dose of the drug through the exit ports 28 and out of the device 12. In the presently preferred embodiment, the drug delivery chamber 20 is expanded from a collapsed condition to an expanded condition, wherein each time the drug delivery chamber 20 is expanded, a dose of the drug is delivered. In addition, as the drug delivery chamber 20 expands, the drug delivery chamber 20 fills the drug storage chamber 18. That is, the chamber 20 replaces the volume of the drug storage chamber 18 previously occupied by the dose of the drug which was forced out of the drug storage chamber 18. For example, in an initial state, the drug storage chamber 18 is preferably filled with the drug such that the drug delivery chamber 20 occupies a relatively small space therein and in a final state, the drug storage chamber 18 has little or no drug left therein and the drug delivery chamber 20 occupies a significant or substantially the entire volume of the drug storage chamber 18. In the preferred embodiment, the drug delivery chamber 20 is a flaccid bag which expands or grows within the drug storage chamber 18 as the gas fills the drug delivery chamber 20, with the maximum volume of the bag being substantially equal to the volume of the drug storage chamber 18.

The drug delivery chamber 20 is preferably constructed of a resilient, flexible material which will not break or stretch beyond predetermined limits, such as a membrane constructed of a flexible, nonreactive material with a high modulus of elasticity to insure successful release of all of the doses of the drug from the drug storage chamber 18, such as medical grade silicone rubber. Other suitable materials for constructing such an inflatable membrane are well known to those of ordinary skill in the art.

The gas pressurized chamber 22 is located adjacent to the drug storage chamber 18 and the drug delivery chamber 20. The gas pressurized chamber 22 comprises a sealable chamber for holding a predetermined amount of a predetermined gas under pressure. The gas pressurized chamber 22 is connected to the drug delivery chamber 20 by way of a valve 32. The valve 32 has an open position in which pressurized gas is allowed to pass from the gas pressurized chamber 22 to the drug delivery chamber 20 and a normally closed position in which the gas is sealed within the gas pressurized chamber 22. Thus, when the valve 32 is in the open position, the gas stored in the gas pressurized chamber 22 escapes into the drug delivery chamber 20, causing the delivery chamber 20 to expand, which in turn forces the drug in the drug storage chamber 18 out of the device 12 through the exit ports 28. As previously discussed, the drug delivery chamber 20 is expanded enough to force one dose of the drug out of the drug storage chamber 18 at each delivery. Thus, over time, the drug storage chamber 18 is emptied of the drug and the drug delivery chamber 20 is filled with the gas (inflated) until the chamber 20 fills the space within the drug storage chamber 18 previously occupied by the drug.

Alternatively, the drug delivery chamber 20 could comprise an inflatable/deflatable membrane and the valve 32 could include a pressure release mechanism (not shown) which allows the drug delivery chamber 20 to deflate or return to a static condition when the valve 32 returns to the closed position from the open position. Such release mechanisms are well known. For example, the release mechanism could be an integral part of the valve 32 or the valve 32 could be a three-way valve, as is known to those of ordinary skill in the art.

The size of the gas pressurized chamber 22 depends on, among other things, the volume of gas stored in the chamber 22, which in turn depends on the volume of the drug stored in the drug storage chamber 18 and the size of a dose. The preferred gas is a nontoxic, inert gas. In the presently preferred embodiment, the gas comprises air because air is both safe and ubiquitous. However, other gases may be used, generally without limitation, so long as the gas is generally nontoxic to humans and rechargeable, such as nitrogen, oxygen and carbon dioxide. The pressure of the gas in the gas pressurized chamber 22, after the device 12 has been charged (i.e. when the gas is loaded into the chamber 22), is about 1.2 to about 2.5 atmospheres of absolute pressure.

The gas pressure chamber 22 includes an inlet port 34 through which gas may be delivered into the gas pressurized chamber 22, such as with a needle, as is known to those of ordinary skill in the art. This allows the gas pressurized chamber 22 to be recharged once the gas pressure within the chamber 22 falls below a predetermined minimum pressure, which minimum pressure is the pressure required to deliver one dose of the drug.

The valve 32 is preferably a normally closed, electric solenoid valve which does not allow the pressurized gas to escape or leak from the gas pressurized chamber 22 when the valve 32 is in the closed position. That is, the valve 32 should have a zero leakage rate. The valve 32 should also have a response time on the order of 3 msec and operate with low voltage and current. Subminiature solenoid valves are generally commercially available, for instance from Angar Scientific Company of New Jersey. For a curved, ring shaped housing, such as the housing 16, a curved valve is preferred. If the housing 16 is cylindrical, as opposed to ring shaped, then a straight valve having a cylindrical shape may be used. Alternatively, a microfabricated valve with a zero leakage rate may be used. In a presently preferred embodiment of the invention, the valve 32 is about 5 mm to about 10 mm in diameter and about 1 cm to about 2 cm long.

Figure 3:
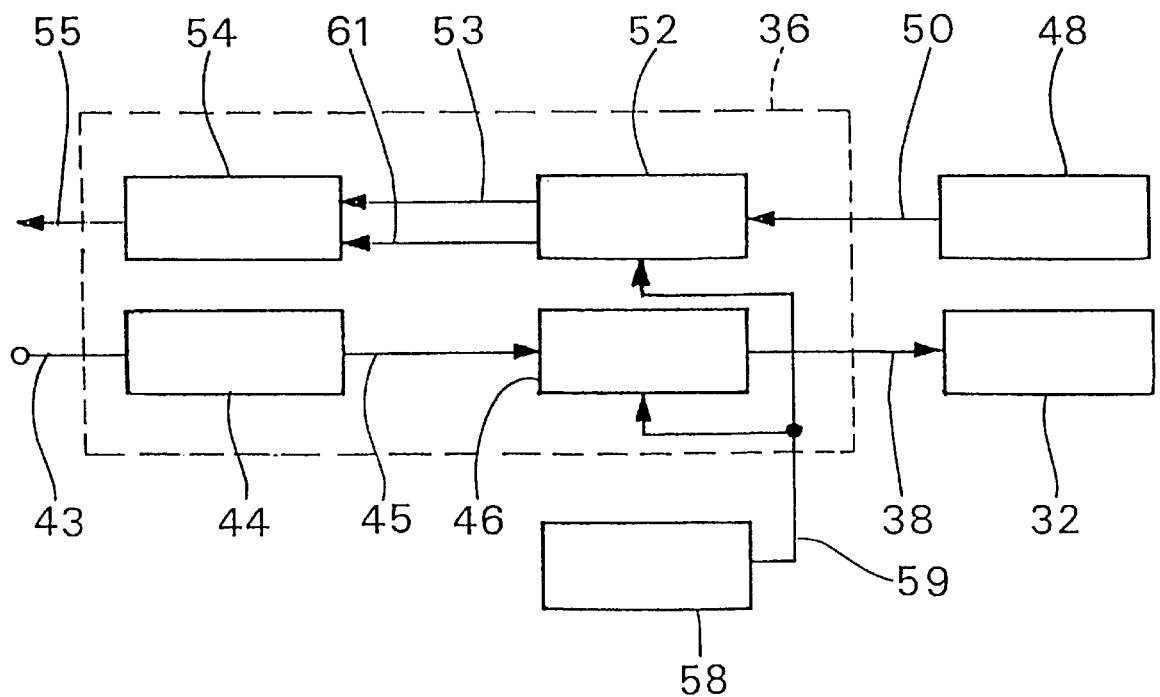
FIG. 3 is a schematic block diagram of a control circuit of the drug delivery system of the present invention.

Referring now to FIGS. 1 and 3, the valve 32 is controlled by an electrical valve open signal generated by a remotely activated control circuit 36, which is electrically connected to the valve 32 by a conductor 38. The control circuit 36 is preferably disposed within the housing 16 in a sealed area 40 proximate to the gas pressurized chamber 22. Alternatively, the control circuit 36 may be disposed within the gas pressurized chamber 22, so that the control circuit 36 is located physically closer to the valve 32, as shown in phantom at 36a and connected to the valve 32 by a conductor 38a.

FIG. 1 shows an exemplary embodiment of the remote signaling device 14 of the present invention. The remote signaling device 14 includes at least one switch, such as an activate button 42. Closing the switch (i.e. depressing the button 42) generates an administer dose signal. The remote signaling device 14 also includes a radio frequency (RF) transmitter circuit (not shown), which modulates and transmits the administer dose signal at a predetermined radio frequency.

The control circuit 36 includes a receiver circuit 44 for detecting and receiving the transmitted administer dose signal. The received administer dose signal is converted to the valve open signal by the control circuit 36 and transmitted to the valve 32 by way of the conductor 38. In FIG. 3, the transmitted administer dose signal is indicated at 43 and the received administer dose signal is indicated at 45. The valve open signal opens the valve 32, which releases the pressurized gas into the drug delivery chamber 20, thereby causing the drug delivery chamber 20 to expand, which in turn forces a dose of the drug through the exit ports 28 and out of the chamber 18. Such transmitter and receiver circuits are well known by those of ordinary skill in the art and readily commercially available. For instance, microreceivers and transmitters are available from Teledyne Corp., of Los Angeles, Calif. For example, similar transmitter and receiver circuits are prevalent in the auto industry, with key fobs including a transmitter and an automobile including a receiver, for remote activation of car door locks and alarm systems. Accordingly, such circuits are not described in detail herein. Suffice it to say that the signaling device 14 provides a means for remote activation of the drug delivery device 12. Moreover, the administer dose signal could be a coded signal to assure that the device 12 does not receive a false signal or a signal from a device other than the remote signaling device 14.

As will be understood by those of ordinary skill in the art, the gas pressure in the gas pressurized chamber 22 decreases each time a dose of the drug is administered. In order to consistently administer the same dose of the drug with each usage, the control circuit 36 preferably includes a timer circuit 46. The timer circuit 36 determines and controls the length of time the valve open signal is asserted or maintained, and thus controls the length of time that the valve 32 remains open. For instance, for a device 12 which is capable of administering thirty doses of the drug, for the initial dose, the valve 32 is opened for a relatively short period of time, as compared to a later administered dose, where the valve 32 is opened for a longer period of time. In the presently preferred embodiment, for an initial dose of the preferred drug C31G, the valve 32 is opened for approximately 3 msec and for a later administered dose of the drug, the valve 32 is opened for approximately 6 msec. However, these times are illustrative only, and the actual length of time that the valve 32 is opened will vary depending upon a number of factors, such as the amount, concentration and viscosity of the drug, the volume of the drug storage chamber 18, the volume of the drug delivery chamber 20, the volume of the pressurized gas chamber 22 and the pressure of the stored gas. Thus, the control circuit 36 controls the volume and flow rate of the gas released into the drug delivery chamber 20. It will be appreciated by those of ordinary skill in the art that the timer circuit 46 could be located in the remote signaling device 14, as opposed to within the device 12 and still control the length of time that the valve 32 is opened.

The drug delivery system 10 further preferably includes means for assuring a user that a dose of the drug was administered and means for determining a remaining number of doses. In the presently preferred embodiment, a pressure transducer 48 is disposed within the gas pressurized chamber 22 and is in communication with the control circuit 36. The pressure transducer 48 monitors the gas pressure within the gas pressurized chamber 22 and transmits a gas pressure signal to the control circuit 36 by way of an electrical conductor 50. The control circuit 36 includes a logic circuit 52 which receives the pressure signal from the pressure transducer 48 and forwards the pressure signal to a control circuit transmitter circuit 54, which modulates the signal received from the logic circuit 52 and transmits the modulated signal, as a dose delivered signal, to the remote signaling device 14. In FIG. 3, the dose delivered signal generated by the logic circuit 52 is indicated at 53 and the transmitted dose administered signal is indicated at 55.

The remote signaling device 14 includes a means for informing the user that the dose was administered, such as by generating an audible tone or displaying a message on a display 56. For instance, the display 56 could be a light, such as an LED, which is illuminated for a short period of time upon receipt of a signal from the control circuit 36. In the presently preferred embodiment, the display 56 comprises a multidigit LCD.

The gas pressure signal may be used, in addition to informing the user that the dose was administered (determined by the change in gas pressure within the gas pressurized chamber 22), to calculate the remaining number of doses which the device 12 is able to administer (determined based upon the remaining gas pressure). In order to maintain a count of the number of doses delivered and/or the number of doses remaining in the device 12, the remote signaling device 14 may include a counter (not shown) which maintains a count of the number of times the dose administered signal is received from the control circuit 36. Such information could then be displayed on the display 56. Accordingly, the remote signaling device 14 includes a display button 62 for activating the display 56 and displaying the number of doses remaining in the device 12. Alternatively, such a counter circuit could be located within the area 40 of the device 12 with the control circuit 36.

The control circuit 36 is connected to a power source, such as a battery 58 located in a battery compartment 60 proximate to the area 40 in which the control circuit 36 is located. The battery 58 preferably has a high electrical density with high energy per unit mass, such as the type of battery used in a hearing aid or a watch. The battery 58 may also be either rechargeable and/or replaceable by the user or a laboratory technician. The battery 58 provides power to the control circuit 36, as indicated by power line 59.

The drug delivery system 10 of the present invention is also capable of providing additional information to a user in the form of a recharge signal, indicated at 61. The recharge signal may comprise a low gas pressure indication, a low power indication signal, and/or a low drug indication signal. For a low power indication signal, the battery 58 is electrically connected to the logic circuit 52, which monitors the charge of the battery 58 and transmits a low-battery signal to the signaling device 14 when the power output of the battery 58 falls below a predetermined minimum value. Thus, the low battery signal indicates to the user that the battery 58 needs to be replaced or recharged. For a low pressure signal, the pressure transducer 48 provides a pressure signal to the logic circuit 52, as previously discussed, with the logic circuit 52 determining when the pressure has fallen below a predetermined minimum pressure value. For a low drug indication signal, the counter in the signaling device 14 provides such information to the user. Such a control circuit 36 including the logic circuit 52 may be readily constructed by one of ordinary skill in the art of electronics without undue experimentation, using commercially available electronic devices. Preferably however, the control circuit 36 comprises an integrated circuit chip.

The housing 16 thus comprises a plurality of individual, connected chambers or sections, including the drug storage 18, the battery compartment 60, the circuit area 40 and the gas pressurized chamber 22. The housing 16 may be constructed as a single unit with internal walls separating the chambers or sections 18, 22, 40, 60, or as multiple individual sections which are joined together. Preferably, if the housing 16 is constructed from multiple separate sections, the sections are joined to each other with flexible joints. It is preferred that the housing 16 is somewhat flexible in order to aid insertion of the device 12 into the body cavity. In the presently preferred embodiment, the housing 16 is constructed from both flexible sections and stiff sections (e.g. the battery compartment 40 and the control circuit area 40, and preferably the drug storage chamber 18), which sections are connected with flexible joints in order to impart sufficient flexibility to the device 12 so that the device 12 is flexible and may be flexed during insertion.

Although a particular embodiment of the present invention has been described, it will be apparent that the present invention may be altered or modified, yet still provide remote controlled drug delivery without departing from the scope and spirit of the invention. Moreover, although the drug delivery system of the present invention is described herein with reference to an intravaginal device, it will be appreciated that such reference to an intravaginal device is provided for illustrative purposes only and is not limiting. The drug delivery system of the present invention is well suited for use in many other types of applications and has application in any area in which the delivery of one or many doses of a drug within a body or body cavity is required. It is understood, therefore, that the present invention is not limited to the particular embodiment disclosed, but is intended to include all modifications and changes which are within the scope and spirit of the invention as defined by the appended claims.

I claim:

1. A drug delivery system comprising:

a housing;

a drug storage chamber located within the housing and having at least one exit port, the drug storage chamber for holding at least one predetermined dose of a predetermined drug;

a drug delivery chamber disposed within the drug storage chamber;

a gas pressurized chamber located within the housing for holding a gas under pressure;

a valve connecting the gas pressurized chamber with the drug delivery chamber, the valve having an open position and a normally closed position, wherein in the open position, the gas is delivered through the valve to the drug delivery chamber;

a remotely activated control circuit electrically connected to the valve for receiving a remotely generated valve open signal and generating an electrical valve open signal therefrom, and providing the electrical valve open signal to the valve; and a signaling device spaced from the control circuit for transmitting the remotely generated valve open signal to the control circuit, wherein upon receipt of the electrical valve open signal, the valve opens such that the gas in the gas pressurized chamber is released into the drug delivery chamber, thereby forcing a predetermined dose of the drug into the at least one exit port and out of the housing.

2. The drug delivery system of claim 1 wherein the housing is sized to fit within a cavity of a human body.

3. The drug delivery system of claim 2 wherein the housing is generally toroidal shaped.

4. The drug delivery system of claim 3 wherein the cavity comprises a vagina and an outer wall of the housing contacts the vaginal wall.

5. The drug delivery system of claim 4 wherein the housing has an outer diameter of about 40 mm to about 80 mm and an inner diameter of about 25 mm to about 75 mm.

6. The drug delivery system of claim 4 wherein the drug storage chamber contains a drug, wherein the drug comprises a microbicide.

7. The drug delivery system of claim 6 wherein the drug has an activity selected from the group comprising spermicidal, antiviral, antibacterial, antifungal, anticonceptive and antisexually transmitted disease activities, and mixtures thereof.

8. The drug delivery system of claim 7 wherein the drug comprises a compound comprising as a first component an alkyl-N-betaine surfactant and as a second compound an oxide selected from the group consisting of alkyl-N, N-dimethyl amine oxide, N-dihydroxyethylamine oxide, acylamino t-amine oxide and mixtures thereof.

9. The drug delivery system of claim 6 wherein the drug comprises a C31G.

10. The drug delivery system of claim 4 wherein a plurality of predetermined doses of the drug are stored in the drug storage chamber.

11. The drug delivery system of claim 10 wherein the plurality comprises at least ten.

12. The drug delivery system of claim 1 wherein the housing is constructed of a flexible, biocompatible material.

13. The drug delivery system of claim 1 wherein the pressurized gas is nontoxic.

14. The drug delivery system of claim 13 wherein the pressurized gas comprises air.

15. The drug delivery system of claim 1 wherein the gas pressure is about 1.2 atmospheres to about 2.5 atmospheres of absolute pressure.

16. The drug delivery system of claim 1 wherein the gas pressure chamber is rechargeable.

17. The drug delivery system of claim 1 wherein the drug delivery chamber comprises a collapsible membrane.

18. The drug delivery system of claim 1 wherein each one exit port comprises a slit in an outer surface of the housing and an inner surface of the drug storage chamber, wherein the drug passes through the slit only when the pressurized gas is released into the drug delivery chamber.

19. The drug delivery system of claim 1 wherein the valve comprises a solenoid valve.

20. The drug delivery system of claim 1 wherein the control circuit includes a timer circuit for maintaining the electrical valve open signal for a predetermined time period.

21. The drug delivery system of claim 20 wherein the electrical valve open signal is maintained for at least 3 msec.

22. The drug delivery system of claim 1 further comprising a pressure transducer disposed within the gas pressurized chamber and in communication with the control circuit, wherein the pressure transducer monitors the gas pressure within the gas pressurized chamber and transmits a gas pressure signal to the control circuit.

23. The drug delivery system of claim 22 wherein the control circuit further comprises:

means for generating a dose delivered signal; and a control circuit transmitter for transmitting the dose delivered signal to the signaling device, wherein the signaling device includes means for displaying the transmitted dose delivered signal.

24. The drug delivery system of claim 23 wherein the control circuit further comprises:

means for generating a recharge signal, wherein the recharge signal is transmitted to the signaling device by the control circuit transmitter.

25. The drug delivery system of claim 24 wherein the signaling device includes means for displaying the transmitted recharge signal.

26. The drug delivery system of claim 24 wherein the recharge signal indicates a low gas pressure condition within the gas pressurized chamber.

27. The drug delivery system of claim 24 wherein the recharge signal indicates a low power condition of a control circuit power source.

28. The drug delivery system of claim 24 wherein the recharge signal indicates a low drug condition within the drug storage chamber.

29. The drug delivery system of claim 24 wherein the recharge signal indicates a low gas pressure condition within the gas pressurized chamber, a low power condition of a control circuit power source, and a low drug condition within the drug storage chamber.

30. A drug delivery system comprising:

a housing;

a drug storage chamber located within the housing having at least one exit port, the drug storage chamber adapted to hold at least one predetermined dose of a predetermined drug;

a drug delivery chamber disposed within the drug storage chamber;

a gas pressurized chamber located within the housing for holding a nontoxic gas under pressure;

a valve connecting the gas pressurized chamber with the drug delivery chamber, the valve having an open position and a closed position, wherein in the open position, the gas is delivered through the valve to the drug delivery chamber, thereby forcing one dose of the drug out of the exit port;

a pressure transducer located within the gas pressurized chamber for monitoring the gas pressure therein and generating a corresponding gas pressure signal;

a signaling device spaced from the housing for generating a valve open signal and transmitting the valve open signal at a predetermined radio frequency; and a remotely activated control circuit located within the housing, the control circuit including a receiver circuit, a timer circuit, and a transmitter circuit, the receiver circuit for receiving the transmitted valve open signal, the timer circuit receiving the transmitted valve open signal from the receiver circuit, generating an electrical valve open signal, and providing the electrical valve open signal to the valve for a predetermined time period, and the transmitter circuit for receiving the gas pressure signal from the pressure transducer, generating a dose delivered signal therefrom, and transmitting the dose delivered signal to the signaling device, wherein the signaling device includes a display for displaying the dose delivered signal.

31. An intravaginal drug delivery device comprising:

a generally toroid shaped housing sized to fit within a human vagina;

a drug storage chamber located within the housing and having at least one exit port, the drug storage chamber for holding a plurality of predetermined doses of a predetermined drug;

a drug delivery chamber comprising a flexible membrane disposed within the drug storage chamber;

a gas pressurized chamber located within the housing for holding a nontoxic gas under pressure;

a valve connecting the gas pressurized chamber with the drug delivery chamber, the valve having an open position and a closed position, wherein in the open position, the gas is delivered through the valve to the drug delivery chamber;

a pressure transducer located within the gas pressurized chamber for monitoring the gas pressure therein and generating a corresponding gas pressure signal;

a signaling device spaced from the housing generating a valve open signal and transmitting the valve open signal at a predetermined radio frequency; and a remotely activated control circuit located within the housing, the control circuit including a receiver circuit, a timer circuit, and a transmitter circuit, the receiver circuit for receiving the transmitted valve open signal, the timer circuit receiving the transmitted valve open signal from the receiver circuit, generating an electrical valve open signal, and providing the electrical valve open signal to the valve for a predetermined time period, and the transmitter circuit for receiving the gas pressure signal from the pressure transducer, generating a dose delivered signal therefrom, and transmitting the dose delivered signal to the signaling device, wherein the signaling device includes a display for displaying the dose delivered signal.

* * * * *